United States Patent
Kim et al.

(10) Patent No.: US 9,829,438 B2
(45) Date of Patent: Nov. 28, 2017

(54) HIGH SENSITIVITY BIOSENSOR USING PIXEL ANALYSIS OF CMOS IMAGE SENSOR

(71) Applicant: GWANGJU INSTITUTE OF SCIENCE AND TECHNOLOGY, Gwangju (KR)

(72) Inventors: Min-Gon Kim, Gwangju (KR); Hyou-Arm Joung, Gwangju (KR); Dong-Gu Hong, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 560 days.

(21) Appl. No.: 14/388,205

(22) PCT Filed: Nov. 30, 2012

(86) PCT No.: PCT/KR2012/010330
§ 371 (c)(1),
(2) Date: Jan. 6, 2015

(87) PCT Pub. No.: WO2013/147388
PCT Pub. Date: Oct. 3, 2013

(65) Prior Publication Data
US 2015/0116484 A1    Apr. 30, 2015

(30) Foreign Application Priority Data
Mar. 28, 2012    (KR) .................. 10-2012-0031608

(51) Int. Cl.
*H04N 7/18*      (2006.01)
*G01N 21/76*    (2006.01)
(Continued)

(52) U.S. Cl.
CPC ......... *G01N 21/76* (2013.01); *G01N 21/6454* (2013.01); *H04N 5/374* (2013.01)

(58) Field of Classification Search
CPC ..... G01N 21/76; G01N 21/6454; H04N 5/374
See application file for complete search history.

(56) References Cited

U.S. PATENT DOCUMENTS 6,682,900 B1 *  1/2004  Travassos ........ G01N 33/56905
                                                            435/7.1
7,738,086 B2     6/2010  Shepard et al.
(Continued)

FOREIGN PATENT DOCUMENTS

KR    1020090081266 A    7/2009

OTHER PUBLICATIONS

Frederic Mallard et al., Opto-electronic DNA chip: high performance chip reading with an all-electric interface, article, 2005, pp. 1813-1820, Elsevier, Science Direct, Biosensors and Bioelectronics 20.
(Continued)

*Primary Examiner* — Nhon Diep
(74) *Attorney, Agent, or Firm* — Hauptman Ham, LLP

(57) ABSTRACT

Provided are a method of analyzing a target substance to be measured, the method including: dividing a surface of a measuring unit of a CMOS image sensor into a plurality of pixels, directly fixing a bioreceptor onto the surface of the measuring unit of the CMOS image sensor, and measuring chemiluminescent signals depending on concentrations of the target substance to be measured, and a CMOS image sensor applied to the same.

5 Claims, 6 Drawing Sheets

(51) Int. Cl.
    *G01N 21/64*    (2006.01)
    *H04N 5/374*    (2011.01)

(56)            References Cited

U.S. PATENT DOCUMENTS

| | | | |
|---|---|---|---|
| 8,021,848 B2 | 9/2011 | Straus | |
| 2003/0227612 A1 | 12/2003 | Fein et al. | |
| 2005/0181516 A1* | 8/2005 | Dressman | C12Q 1/6883 |
| | | | 436/161 |
| 2005/0190286 A1 | 9/2005 | Kaduchak et al. | |
| 2008/0081769 A1 | 4/2008 | Hassibi | |
| 2008/0124327 A1* | 5/2008 | Young | A61K 47/48561 |
| | | | 424/133.1 |
| 2011/0027796 A1* | 2/2011 | An | C12Q 1/6886 |
| | | | 435/6.11 |
| 2011/0091870 A1 | 4/2011 | Lang et al. | |
| 2012/0105786 A1* | 5/2012 | Iwamoto | G02F 1/13378 |
| | | | 349/139 |
| 2014/0113404 A1* | 4/2014 | Rossini | H01L 27/14632 |
| | | | 438/98 |

OTHER PUBLICATIONS

International Search Report for PCT/KR2012/010330 dated Mar. 25, 2013.

* cited by examiner

Unit: fg/ml

HIGH SENSITIVITY BIOSENSOR USING PIXEL ANALYSIS OF CMOS IMAGE SENSOR

TECHNICAL FIELD

The present invention relates to a CMOS image sensor maximizing detection sensitivity in the same reaction signal by measuring and analyzing chemiluminescent signals depending on reaction concentrations of a target substance to be measured as a pixel unit of the CMOS image sensor, on a substrate of the CMOS image sensor having a bioreceptor fixed thereonto, and more specifically, to a CMOS image sensor capable of maximizing the detection sensitivity by directly analyzing the signal of each pixel arrangement in a measurement region and measuring the number of pixels having a cut-off value or more.

BACKGROUND ART

A biochip is a biosensor technology in which several tens to several tens of thousands different analysis substances are fixed onto a solid surface, and a specific signal is analyzed by using an analysis equipment to be utilized in a wide range of fields such as a biolabeling substance screening, a disease diagnosis, an environment monitoring, and the like. Examples of a substrate used in a biochip include a silicone wafer, a hydrogel (*PerkinElmer Life sci*), a hybond ECL membrane (*Anal. Biochem*, 294, 55, 2001), a glass surface, a thin-film NC slide (*J. Biomol. Technol*, 18, 245, 2007), a photonic crystal surface, an NC slide, and the like, and a method of fixing a target substance onto a surface by using an adsorption method and a covalently bonding method has been known.

The biochip is measured by fixing different biosubstances onto a surface of a sensor into which a reactor capable of fixing the biosubstances is introduced, and reacting the biosubstances with an analysis substance to react a secondary reaction substance having a labeled specific substance, and using an analysis equipment. As a method of manufacturing a multiple analysis of biochip, methods such as a microarray, a light patterning, and the like, have been used. As the labeling substance, various labeling substances in addition to enzymes, luminescences, fluorescent nanoparticles, metal nanoparticles, and quantum dot have been used. In addition, various kinds of measuring systems such as a fluorescent scanner, a SPR biosensor, a light absorption sensor, and the like, depending on a labeling shape and the surface have been involved.

The biochip which is the most widely used for disease diagnosis, new medicine development, or the like, is a diagnosis sensor fixing antibody or antigen protein onto the surface of the sensor to screen a candidate substance or to diagnose the occurrence of a specific disease in a patient sample. However, a detection sensitivity of the biochip researched up to now is several pg/ml to several tens of pg/ml, and thus, it is not possible to analyze a biomarker having a concentration of a pg/ml unit or less in a human body. As an example, in the case of cytokine intermediating signal transmission between cells among important biomarkers present in the human body, most of cytokine is present at a concentration of a pg/ml unit or less, such that it is almost impossible to analyze the cytokine by using biochip technologies. In addition, since most of the existing analysis equipments analyzing the biochips, such as a fluorescent scanner, a SPR sensor, and the like, are slightly expensive, economic feasibility of the measuring equipments is an important problem to be solved. Therefore, in order to implement development of more advanced biomarkers, screening of new medicine candidate substances, disease diagnosis, and the like, through the biochip technology, development of a new biochip technology capable of having economic feasibility and achieving high sensitivity measurement as compared to the existing technologies is urgently needed.

In order to improve the detection sensitivity of the biochip, a method of improving the detection sensitivity of a label system to be used and an effective signal analysis system are required. A chemiluminescence method has been known as an ultra high sensitivity detection method showing detection sensitivity of a zeptomole ($10^{-18}$ to $10^{-21}$ mole) level in an immune reaction (*Clin Biochem*, 26, 325, 1993). Recently, an example of applying the chemiluminescence method to a diagnostic sensor such as a high sensitivity strip sensor has been gradually increased (*BioChip J.* 4(2), 155, 2010).

A number of patents such as U.S. Pat. No. 8,021,848, U.S. Patent Application Publication No. 2005/0190286 reported a number of sensors such as bioimaging using a CMOS image sensor, a fluorescent sensor, a magnetic sensor, and the like.

However, development of the biosensor having excellent detection sensitivity and improved light sensitivity of the sensor as compared to the measurement method has been continuously required.

DISCLOSURE

Technical Problem

Accordingly, the present inventors made an effort to develop a high sensitivity measuring method capable of analyzing trace amounts of a sample which is difficult to be analyzed by the existing sensing technology, and as a result, found that when chemiluminescent is achieved by dividing a surface of a measuring unit of a CMOS image sensor into each pixel and directly fixing a bioreceptor onto a surface of the measuring unit of the CMOS image sensor, an sensitive efficiency of the image sensor may be increased, thereby completing the present invention.

Therefore, an object of the present invention is to provide a method of measuring a concentration of a target substance to be measured, by using the CMOS image sensor having the bioreceptor directly fixed onto the surface of the measuring unit.

Technical Solution

In order to achieve the object of the present invention, in one general aspect, there is provided a method of measuring a concentration of a target substance to be measured by using a CMOS image sensor, the method including: dividing a surface of a measuring unit of the CMOS image sensor into each pixel, fixing a bioreceptor onto the surface of the measuring unit of the CMOS image sensor, and analyzing a chemiluminescent signal at each pixel.

In addition, in another general aspect, there is provided a CMOS image sensor including a measuring unit having a bioreceptor fixed onto a surface divided into each pixel.

Advantageous Effects

According to the present invention, measurement sensitivity may be increased by using a CMOS image sensor itself as a substrate for fixing a bioreceptor, and measuring light intensity in a luminescent reaction in a state in which the substrate is adjacent to the sensor itself to analyze variables of each pixel.

In addition, since trace amounts of the biomarker which is difficult to be measured in a protein chip, and the like, of the related art, may be analyzed and screened by using the analysis method according to the present invention, the analysis method of the present invention may be applied to develop new medicines and new biomarkers.

Further, instead of a high cost analysis equipment used for analysis of the protein chip in the related art, a high sensitivity biosensor having small size and low manufacturing cost may be implemented to be applied as an economical biochip analysis system.

| [Detailed Description of Main Elements] | |
|---|---|
| 10: CMOS Image Sensor | 11: Measuring Unit |
| 12: Connecting Unit | 21: STA-HRP |
| 22: IL-5 Capture Antibody | 23: IL-5 Antigen |
| 24: IL-5 Detection Antibody | 25: HRP |

BEST MODE

The present invention is characterized by a method of measuring a concentration of a target substance to be measured by using a CMOS image sensor, including dividing a surface of a measuring unit of a CMOS image sensor into a plurality of pixels, fixing a bioreceptor onto the surface of the measuring unit of the CMOS image sensor, and analyzing a chemiluminescent signal at each pixel.

In addition, the present invention is characterized by a CMOS image sensor including a measuring unit having a bioreceptor fixed onto a surface divided into a plurality of pixels.

Figure 1:
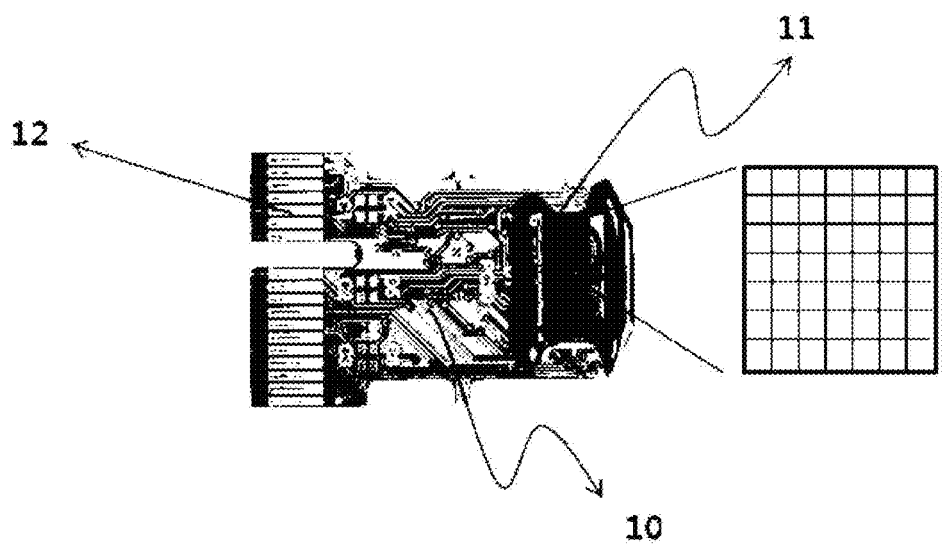
FIG. 1 is a schematic diagram of a CMOS image sensor according to the present invention.

FIG. 1 is a schematic diagram of a strip CMOS image sensor according to an exemplary embodiment of the present invention. As shown in FIG. 1, the CMOS image sensor 10 includes the measuring unit 11 and a sensor connecting unit 12. The measuring unit 11 serves to sense a chemiluminescent signal, and the sensor connecting unit 12 serves to connect a measuring instrument with a sensor.

The surface of the measuring unit is divided into a plurality of pixels, wherein the pixel preferably has a size of 0.01 to 100 $\mu m^2$, and more preferably, a size of 0.1 to 50 $\mu m^2$, but the number and the size of pixels may be appropriately adjusted depending on substances to be measured.

In addition, a reactor may be introduced onto the surface of the measuring unit by various methods, and various kinds of bioreceptors may be fixed onto the surface of the sensor into which the reactor is introduced to thereby be used as a biochip. As the bioreceptor, at least one kind selected from the group consisting of antibodies, DNAs, enzymes, aptamers, peptide nucleic acids (PNAs), and ligands may be used.

Meanwhile, in the present invention, a target substance to be measured may be at least one kind selected from the group consisting of enzymes, proteins, DNAs, RNAs, microorganisms, animal and plant cells and organs, wherein the enzymes may be peroxidase, phosphatase, or luciferase.

A chemiluminescent reaction is used in order to analyze a signal of the target substance reacting with the bioreceptor fixed onto the surface of the measuring unit. In order to induce the chemiluminescent reaction, the chemiluminescent substance may be preferably luminol, isoluminol, luciferin, lucigenin, 3-(2'-Spiroadamantane)-4-methoxy-4-(3"-phosphoryloxy)phenyl-1,2-dioxetane (AMPPD), disodium 3-(4-methoxyspiro {1,2-dioxetane-3,2'-(5'-chloro)tricyclo[3.3.1.13,7]decan}-4-yl)phenyl phosphate (CSPD), and the like, but the present invention is not limited thereto. The chemiluminescent substance may be appropriately selected by a person skilled in the art.

The concentration of the target substance to be measured is determined by analyzing the chemiluminescent signal at each pixel on the surface of the measuring unit.

Here, 1) the concentration of the target substance to be measured may be determined by selecting a cut-off value of the chemiluminescent signal, and measuring the number of pixels indicating signals having the cut-off value or more.

In addition, 2) the concentration of the target substance to be measured may be determined by selecting a cut-off value of the chemiluminescent signal, and measuring the number of pixels showing signals in which a difference in signal intensity between before and after performing a chemiluminescent reaction has the cut-off value or more.

The cut-off value may be appropriately adjusted and selected depending on the substance to be measured, measurement items or measurement methods.

As compared to general methods of measuring chemiluminescent intensity, the measurement method using the CMOS image sensor of the present invention may maximize the detection sensitivity, and a distance between the chemiluminescent signal of the target substance reacted with the fixed bioreceptor and the sensor is about several nm, such that the sensor is advantageous to induce the chemiluminescent signal.

In particular, the measurement method using the CMOS image sensor is characterized by analyzing the number of pixels indicating signals having the cut-off value or more at each pixel. For example, in the case in which a difference in signal intensity between before and after performing the chemiluminescent reaction is shown in 1 to 2 pixels among 1000 pixels, when converting the difference into an average light intensity of 1000 pixels, the converted value is not meaningless; however, when analyzing the number of each pixel having difference in signal, the number is meaningful.

The above described aspects and additional aspects of the present invention will be more clearly described by preferred exemplary embodiments with reference to the accompanying drawings. Hereinafter, the present invention will be described in detail by these exemplary embodiments so that a person of ordinary skilled in the art can easily understand and realize the present invention.

However, the following examples are provided only for exemplifying the present invention, and it will be obvious to those skilled in the art that the scope of the present invention is not construed to be limited to these examples.

Example 1 Measurement of Streptavidin-Horseradish Peroxidase (STA-HRP)

46000 pixels having each width of about 4 μm and each length of about 4 μm, were formed on the surface of the measuring unit 11 of the CMOS image sensor of FIG. 1. A solution (concentration of 0, 1, 100, 10000 fg/ml) obtained by dissolving streptavidin-horseradish peroxidase (STA-HRP) manufactured by Calbiochem, USA in 10 mM PB buffer (pH 7.0) was reacted onto the surface of the measuring unit modified by a biotin group at room temperature for 30 minutes, to fix enzymes onto the surface by an adsorption method. Then, the surface was washed with 10 mM PB buffer, distilled water, and 0.1M carbonate buffer (pH 9.0) in sequence.

Next, the measuring unit was treated with 2 mM luminol dissolved in 0.1M carbonate buffer (pH 9.0) and 2 mM hydrogen peroxide solution.

Figure 2:
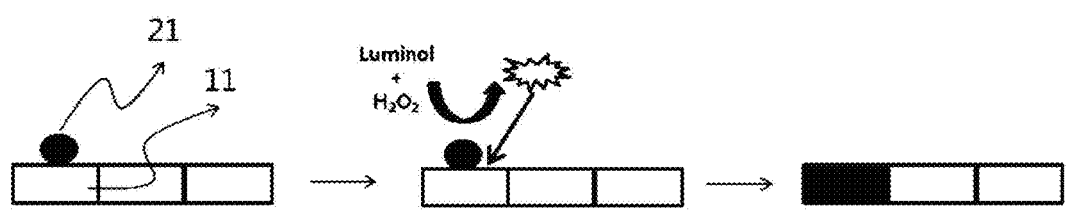
FIG. 2 shows a process measuring a chemiluminescent signal by fixing streptavidin-horseradish peroxidase (STA-HRP) in Example 1.

The process of forming the chemiluminescent signal according to the treatment of the luminol and the hydrogen peroxide solution was shown in FIG. 2.

Figure 3:
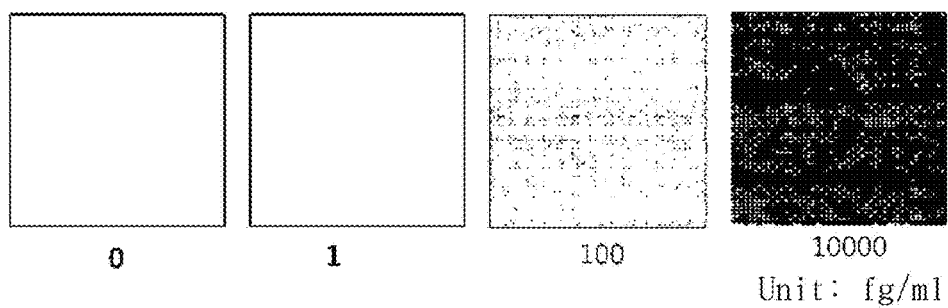
FIG. 3 shows a sensing result obtained by confirming pixels indicating chemilumuminescent signal(s) having a cut-off value or more in Example 1.

After 1 minute elapsed after the treatment, the chemiluminescent signal was measured in a pixel unit, and the cut-off value per each pixel was selected as 10 digits. That is, the number of pixels indicating the chemiluminescent signals having 10 digits or more was measured, and the pixels indicating the chemiluminescent signal having 10 digits or more determined by the measurement method represented as a black color and were shown in FIG. 3.

When the STA-HRP was treated at a concentration of 100 fg/ml, the signal having 10 digits or more was shown in 3,419 pixels, and when the STA-HRP was treated at a concentration of 10,000 fg/ml (10 pg/ml), the signal having 10 digits or more was shown in 19,248 pixels.

Figure 4:
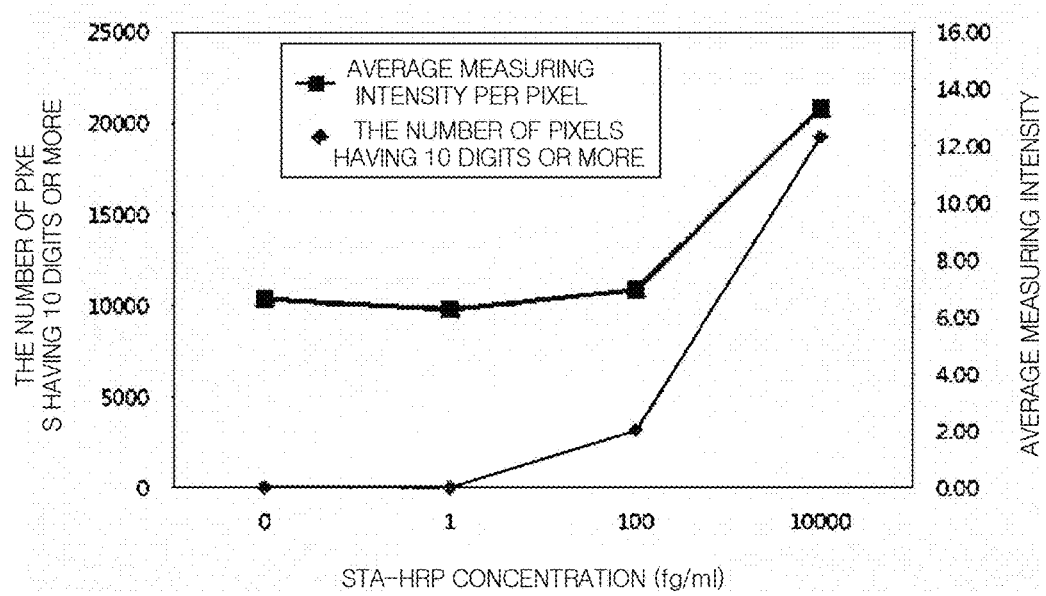
FIG. 4 is a graph showing a result obtained by comparing accuracy between an analysis method of Example 1 and a method of measuring an average intensity of pixels depending on concentrations of streptavidin-horseradish peroxidase (STA-HRP).

In addition, a graph showing a comparison result of average digit values in a measurement region depending on concentrations of streptavidin-horseradish peroxidase (STA-HRP) was shown in FIG. 4.

As shown in the graph of FIG. 4, it could be confirmed that the concentration of the STA-HRP could be measured at high sensitivity by the method of the present invention.

Example 2 Measurement of IL-5

The measuring unit 11 of the CMOS image sensor of FIG. 1 was ultrasonic-washed in 0.1N NaOH solution for 15 minutes, then washed with ethanol three times, and APTMS ((3-Aminopropyl)trimethoxysilane) having 1% concentration dissolved in ethanol was reacted for about 2 hours. Then, the reaction product was washed with ethanol about two times, then ultrasonic washed in ethanol for five minutes again, and dried with high purity nitrogen gas. In addition, in order to prepare a surface reacting with an antibody, 2 vol % of glutaraldehyde dissolved in 10 mM PB buffer was reacted for about 4 hours to finally modify the surface of the measuring unit with an aldehyde group.

Then, a 0.1 mg/ml IL-5 capture antibody was reacted onto the modified surface for about 1 hour, followed by reaction with 1% BSA solution for about 2 hours in order to remove non-specific reaction. In addition, IL-5 antigen dissolved in PBS buffer and biotinylated 5 μg/ml IL-5 detection antibody were mixed and reacted for 10 minutes, then reacted on the surface of the measuring unit for 30 minutes to allow an antigen-antibody reaction to proceed, and the surface was washed with PBS buffer and diluted water in sequence. Then, STA-HRP 5 μg/ml dissolved in the PBS buffer was added thereto, followed by reaction for 30 minutes, and washed with PBS buffer, 0.1 M carbonate buffer (pH 9.0) in sequence.

Next, the surface of the measuring unit was treated with 2 mM luminol dissolved in 0.1M carbonate buffer (pH 9.0) and 2 mM hydrogen peroxide solution.

Figure 5:
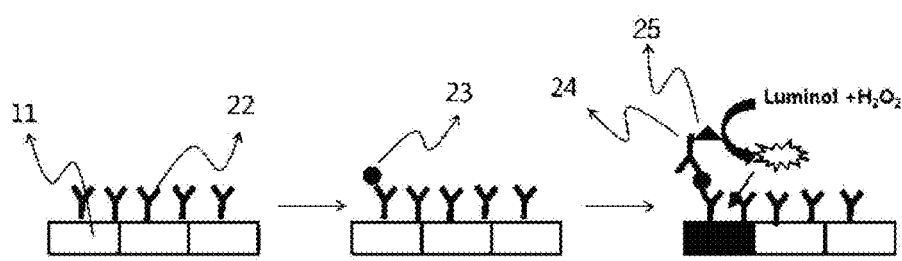
FIG. 5 shows a process of fixing IL-5 in Example 2 and measuring a chemiluminescent signal.

The process of forming the chemiluminescent signal depending on treatment of the luminol and the hydrogen peroxide solution was shown in FIG. 5.

Figure 6:
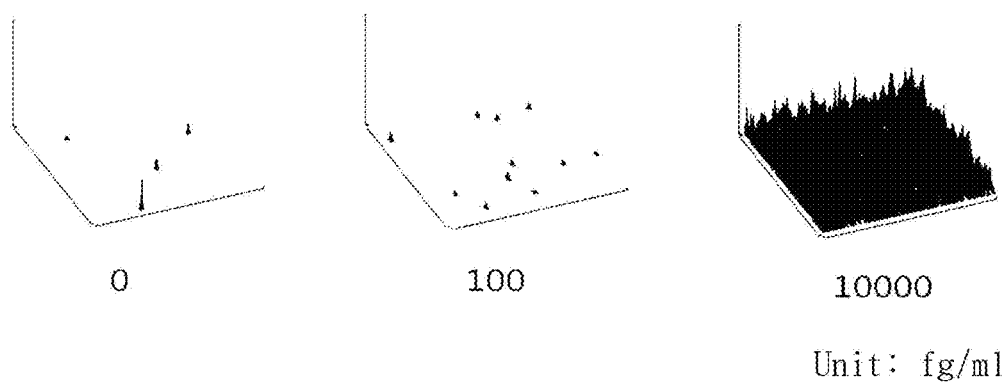
FIG. 6 shows a sensing result obtained by three-dimensionally confirming pixels indicating chemiluminescent signals having a cut-off value or more in Example 1.

After 1 minute elapsed after the treatment, the difference in the chemiluminescent signal between before and after treating the luminol and the hydrogen peroxide solution was measured. The cut-off value per pixel was selected as 2 digits, and the number of pixels in which a difference in signal intensity between before and after performing the chemiluminescent reaction had the cut-off value or more was measured. FIG. 6 is a three-dimensional image of pixels having the cut-off value or more, an increase in signal having 2 digits or more was shown in 3 pixels when the concentration of the IL-5 antigen is 0, in 11 pixels when the concentration of the IL-5 antigen is 100 fg/ml, and in 4069 pixels when the concentration thereof is 10,000 fg/ml (10 pg/ml).

Therefore, it could be confirmed that quantitative analysis of IL-5 could be conducted by the method of the present invention.

Although specific embodiments of the present invention are described in detail as described above, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A method of measuring a concentration of a target substance to be measured by using a CMOS image sensor, the method comprising:
   dividing a surface of a measuring unit of the CMOS image sensor into a plurality of pixels;
   fixing a bioreceptor onto the surface of the measuring unit of the CMOS image sensor;
   analyzing a chemiluminescent signal at each pixel;
   determining the number of pixels that receive the chemiluminescent signal equal to or stronger than a predetermined cut-off value; and
   determine the concentration of the target substance based on the determined number of pixels that receive the chemiluminescent signal equal to or stronger than the predetermined cut-off value.

2. The method of claim 1, wherein analyzing the chemiluminescent signal at each pixel comprises determining a difference in chemiluminescent signal strength before and after a chemiluminescent reaction.

3. The method of claim 1, wherein the pixel has a size of 0.01 to 100 μm$^2$.

4. The method of claim 1, wherein the target substance to be measured is at least one kind selected from the group consisting of enzymes, proteins, DNAs, RNAs, microorganisms, animal and plant cells and organs.

5. The method of claim 1, wherein the bioreceptor is at least one kind selected from the group consisting of antibodies, DNAs, enzymes, aptamers, peptide nucleic acids (PNAs), and ligands.

\* \* \* \* \*